United States Patent [19]

LaBean et al.

[11] Patent Number: 5,869,295

[45] Date of Patent: *Feb. 9, 1999

[54] METHODS AND MATERIALS FOR PRODUCING GENE LIBRARIES

[75] Inventors: Thomas H. LaBean, Philadelphia; Tauseef R. Butt, Audubon, both of Pa.

[73] Assignees: The Trustees of University of Pennsylvania, Philadelphia; SmithKline Beecham Corporation, King of Prussia, both of Pa.

[ * ] Notice: The term of this patent shall not extend beyond the expiration date of Pat. No. 5,656,467.

[21] Appl. No.: 771,201

[22] Filed: Dec. 20, 1996

Related U.S. Application Data

[62] Division of Ser. No. 389,679, Feb. 15, 1995, Pat. No. 5,656,467, which is a continuation of Ser. No. 184,367, Jan. 21, 1994, abandoned, which is a continuation of Ser. No. 819,354, Jan. 9, 1992, abandoned.

[51] Int. Cl.$^6$ ............................ C12N 15/64; C12P 19/34; C07H 21/04
[52] U.S. Cl. ................... 435/91.2; 435/91.1; 435/172.3; 435/320.1; 536/23.1; 536/23.4
[58] Field of Search ................... 435/91.1, 91.2, 435/172.3, 320.1; 536/23.1, 23.4

[56] References Cited

U.S. PATENT DOCUMENTS

| | | | |
|---|---|---|---|
| 4,683,202 | 7/1987 | Mullis | 435/91.2 |
| 5,223,409 | 6/1993 | Ladner et al. | 435/69.7 |
| 5,270,163 | 12/1993 | Gold et al. | 435/6 |
| 5,316,922 | 5/1994 | Brown et al. | 435/69.7 |
| 5,656,467 | 8/1997 | LaBean et al. | 435/172.3 |

FOREIGN PATENT DOCUMENTS

WO86/05803  10/1986  WIPO .

OTHER PUBLICATIONS

Butt et al., PNAS, 86: 2540–2544, 1989.
Edgington, Bio/Technology, 11: 285–289, 1993.
Kauffman, J. Theor. Biol., 157: 1–7, 1992.
LaBean et al., Protein Science, 2: 1249–1254, 1993.
Scott, TIBS, 17: 241–245, 1992.
Shatzman et al., Methods in Enzymology, 152: 661–673, 1987.
Sjostrom et al., J. Mol. Evol., 22: 272–277, 1985.
Waller, J. Mol. Biol., 7: 483–496, 1967.
Yoo et al., J. Biol. Chem., 264:17078–17083, 1989.
Arkin et al., Bio/Technology 10: 297–300, 1992.
Bachmair et al., Science, 234: 179–186, 1986.
Cwirla et al., PNAS, 87:6378–6382, 1990.
Devlin et al., Science, 249: 404–406, 1990.
Ecker et al., J. Biol. Chem., 262; 14213–14221, 1987.
Edgington, Bio/Technology, 10: 137–140, 1992.
Ellington et al., Nature, 346: 818–822, 1990.
Geysen et al., PNAS, 81: 3998–4002, 1984.
Hodgson, Bio/Technology, 8: 1245–1247, 1990.
Horwitz et al., J. Biol. Chem., 263: 14724–14731, 1988.
Kaiser et al., Science, 235: 312–317, 1987.
Klapper, Biochem. Biophys. Res. Com., 78: 1018–1024, 1977.
Kolaskar et al., Int. J. Peptide Protein Res., 22: 1018–1024, 1983.
LaBean et al., The FASEB J., Abstract, ASBMB/Biophysical Meeting, vol. 6, No. 1, 1992.
Ma et al., Cell, 51: 113–119, 1987.
Mandecki, Protein Engineering, 3: 221–226, 1990.
Monia et al., J. Biol. Chem., 264: 4093–4103, 1989.
Oliphant et al., Nucleic Acids Res., 16: 7673–7683, 1988.
Parmley et al., Gene, 73: 305, 1988.
Scott et al., Science, 249: 386–390, 1990.
Tuerk et al., Science, 249, 505–510, 1990.
Vonderviszt et al., Int. J. Peptide Protein Res., 27: 483–492, 1986.

*Primary Examiner*—Nancy Degen
*Attorney, Agent, or Firm*—Brinks Hofer Gilson & Lione

[57] ABSTRACT

Methods for producing libraries of diverse nucleotide sequences, and libraries of polypeptides encoded thereby, are provided. The nucleotide sequences comprise a first and a second constant region coupled to a coding sequence, wherein the coding sequence is formed by sequentially coupling nucleotides in a mixture of predetermined proportions of A, T, C, and G based upon a known amino acid profile. Libraries of vectors comprising the diverse nucleotide sequences are also provided. DNA and amino acid sequences encoding the libraries are further provided.

13 Claims, 5 Drawing Sheets

FIG. I

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

C G G A A T T C C T  A G A C G T         1 6

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

A G C A G G A T C C  C T T C G A A         1 7

( 2 ) INFORMATION FOR SEQ ID NO:3:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:3:

ACGCACTTGC CGAGATCT                                                                                     18

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

CGCGGGTACC TCTACGGATC C                                                                                 21

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CTTGTCTTAA GACTAAGAGG TGGT                                                                              24

( 2 ) INFORMATION FOR SEQ ID NO:6:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 6..83

( x i ) SEQUENCE DESCRIPTION: SEQ ID NO:6:

AGCAG GAT CCC TTC GAA NNN NNN NNN NNN NNN NNN NNN NNN NNN NNN                                            47
      Asp Pro Phe Glu Xaa Xaa Xaa Xaa Xaa Xaa Xaa Xaa Xaa Xaa
      1               5                       10

NNN NNN NNN NNN NNN NNN NNN NNN NNN NNN NNN GTC TAGGAATTCC                                               93
Xaa Xaa Xaa Xaa Xaa Xaa Xaa Xaa Xaa Xaa Xaa Val
 15                  20                      25

G                                                                                                        94

( 2 ) INFORMATION FOR SEQ ID NO:7:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 14..118

( x i ) SEQUENCE DESCRIPTION: SEQ ID NO:7:

```
ACGCACTTGC CGA GAT CTN NNN NNN NNN NNN NNN NNN NNN NNN NNN NNN          49
           Asp Leu Xaa Xaa Xaa Xaa Xaa Xaa Xaa Xaa Xaa Xaa
           1           5                       10

NNN NNN NNN NNN NNN NNN NNN NNN NNN NNN NNN NNN NNN NNN NNN NNN         97
Xaa Xaa Xaa Xaa Xaa Xaa Xaa Xaa Xaa Xaa Xaa Xaa Xaa Xaa Xaa Xaa
        15                      20                      25

NNN NNN NNN NNN NNG GAT CCG TAGAGGTACC CGCG                             132
Xaa Xaa Xaa Xaa Xaa Asp Pro
        30              35
```

( 2 ) INFORMATION FOR SEQ ID NO:8:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 25..138

( x i ) SEQUENCE DESCRIPTION: SEQ ID NO:8:

```
CTTCTCTTAA GACTAAGAGG TGGT NNN NNN NNN NNN NNN NNN NNN NNN NNN          51
                          Xaa Xaa Xaa Xaa Xaa Xaa Xaa Xaa Xaa
                          1               5

NNN NNN NNN NNN NNN NNN NNN NNN NNN NNN SNN NNN NNN NNN NNN NNN         99
Xaa Xaa Xaa Xaa Xaa Xaa Xaa Xaa Xaa Xaa Xaa Xaa Xaa Xaa Xaa Xaa
10                  15                      20                      25

NNN NNN NNN NNN NNN NNN NNN NNN NNN NNN NNG GAT CCG TAGAGGTACC          148
Xaa Xaa Xaa Xaa Xaa Xaa Xaa Xaa Xaa Xaa Xaa Asp Pro
                30                      35

CGCG                                                                    152
```

( 2 ) INFORMATION FOR SEQ ID NO:9:

( i ) SEQUENCE CHARACTERISTICS:
        ( A ) LENGTH: 103 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:9:

```
Met Gln Ile Phe Val Lys Thr Leu Thr Gly Lys Thr Ile Thr Leu Glu
1               5                   10                      15

Val Glu Pro Ser Asp Thr Ile Glu Asn Val Lys Ala Lys Ile Gln Asp
                20                  25                      30

Lys Glu Gly Ile Pro Pro Asp Gln Gln Arg Leu Ile Phe Ala Gly Lys
                35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly Ala Asp Pro Phe
65                  70                  75                      80

Glu Xaa Xaa Xaa Xaa Xaa Xaa Xaa Xaa Xaa Xaa Xaa Xaa Xaa Xaa Xaa
                85                  90                      95
```

```
Xaa  Xaa  Xaa  Xaa  Xaa  Xaa  Val
               100
```

(2) INFORMATION FOR SEQ ID NO:10:

(i) SEQUENCE CHARACTERISTICS:
       (A) LENGTH: 114 amino acids
       (B) TYPE: amino acid
       (C) STRANDEDNESS:
       (D) TOPOLOGY: unknown (ii) MOLECULE TYPE: protein (xi) SEQUENCE DESCRIPTION: SEQ ID NO:10:

```
Met  Gln  Ile  Phe  Val  Lys  Thr  Leu  Thr  Gly  Lys  Thr  Ile  Thr  Leu  Glu
 1              5                        10                            15

Val  Glu  Pro  Ser  Asp  Thr  Ile  Glu  Asn  Val  Lys  Ala  Lys  Ile  Gln  Asp
               20                        25                       30

Lys  Glu  Gly  Ile  Pro  Pro  Asp  Gln  Gln  Arg  Leu  Ile  Phe  Ala  Gly  Lys
          35                        40                       45

Gln  Leu  Glu  Asp  Gly  Arg  Thr  Leu  Ser  Asp  Tyr  Asn  Ile  Gln  Lys  Glu
     50                        55                       60

Ser  Thr  Leu  His  Leu  Val  Leu  Arg  Leu  Arg  Gly  Gly  Xaa  Xaa  Xaa  Xaa
65                        70                       75                       80

Xaa  Xaa  Xaa  Xaa  Xaa  Xaa  Xaa  Xaa  Xaa  Xaa  Xaa  Xaa  Xaa  Xaa  Xaa  Xaa
                    85                        90                       95

Xaa  Xaa  Xaa  Xaa  Xaa  Xaa  Xaa  Xaa  Xaa  Xaa  Xaa  Xaa  Xaa  Xaa  Xaa
               100                       105                      110

Asp  Pro
```

(2) INFORMATION FOR SEQ ID NO:11:

(i) SEQUENCE CHARACTERISTICS:
       (A) LENGTH: 147 amino acids
       (B) TYPE: amino acid
       (C) STRANDEDNESS:
       (D) TOPOLOGY: unknown (ii) MOLECULE TYPE: protein (xi) SEQUENCE DESCRIPTION: SEQ ID NO:11:

```
Met  Gln  Ile  Phe  Val  Lys  Thr  Leu  Thr  Gly  Lys  Thr  Ile  Thr  Leu  Glu
 1              5                        10                            15

Val  Glu  Pro  Ser  Asp  Thr  Ile  Glu  Asn  Val  Lys  Ala  Lys  Ile  Gln  Asp
               20                        25                       30

Lys  Glu  Gly  Ile  Pro  Pro  Asp  Gln  Gln  Arg  Leu  Ile  Phe  Ala  Gly  Lys
          35                        40                       45

Gln  Leu  Glu  Asp  Gly  Arg  Thr  Leu  Ser  Asp  Tyr  Asn  Ile  Gln  Lys  Glu
     50                        55                       60

Ser  Thr  Leu  His  Leu  Val  Leu  Arg  Leu  Arg  Gly  Gly  Xaa  Xaa  Xaa  Xaa
65                        70                       75                       80

Xaa  Xaa  Xaa  Xaa  Xaa  Xaa  Xaa  Xaa  Xaa  Xaa  Xaa  Xaa  Xaa  Xaa  Xaa
                    85                        90                       95

Xaa  Xaa  Xaa  Xaa  Xaa  Xaa  Xaa  Xaa  Xaa  Xaa  Xaa  Xaa  Xaa  Xaa  Xaa
               100                       105                      110

Asp  Leu  Xaa  Xaa  Xaa  Xaa  Xaa  Xaa  Xaa  Xaa  Xaa  Xaa  Xaa  Xaa  Xaa
               115                       120                      125

Xaa  Xaa  Xaa  Xaa  Xaa  Xaa  Xaa  Xaa  Xaa  Xaa  Xaa  Xaa  Xaa  Xaa  Xaa
          130                       135                      140
```

```
Xaa Asp Pro
145
```

METHODS AND MATERIALS FOR PRODUCING GENE LIBRARIES

This application is a division of application Ser. No. 389,679, filed Feb. 15, 1995 and now U.S. Pat. No. 5,656,467, which application was a continuation of application Ser. No. 184,367, filed Jan. 21, 1994 now abandoned, which application was a continuation application of application Ser. No. 819,354, filed Jan. 9, 1992 and now abandoned.

FIELD OF THE INVENTION

The present invention relates generally to methods and materials for producing gene libraries. In particular, the invention relates to methods for producing libraries of diverse nucleotide sequences comprising pre-determined proportions of nucleotides based upon a known amino acid profile. The present invention also relates to libraries of diverse nucleotide sequences produced by these methods and to vectors comprising the libraries. The invention further relates to DNA and amino acid sequences encoding the libraries.

BACKGROUND OF THE INVENTION

The production and screening of libraries of nucleotide sequences has been reported useful for identifying novel peptides, polypeptides, and proteins having a particular biological or chemical property [See Ballivet and Kauffman, PCT application WO 86/05803, published Oct. 9, 1986, incorporated herein by reference]. As explained more fully below, large numbers of diverse DNA and RNA sequences have been screened by various in vitro methods to identify functional biological or chemical molecules such as growth factors, enzymes, and antigens, In the past, randomly selected, genomic DNA was utilized in screening for functional sequences [See Ma and Ptashne, Cell, 51:113–119 (1987); Kaiser, et al., Science, 235:312–317 (1987)]. More particularly, Ma and Ptashne described a class of yeast activators encoded by genes bearing random genomic DNA fragments fused to the coding sequence of the DNA-binding portion of GAL4. It was reported that the activating sequences discovered showed no obvious sequence homology when compared with one another, but manifested the same biological function.

Chemically synthesized random sequence DNA has also been screened for functional properties. A wide variety of functional molecules have been identified from libraries of such random sequences. For example, functional promoter elements have been isolated from populations of randomly synthesized DNA [See Horwitz and Loeb, J. Biol. Chem., 263:14724–14731 (1988); Oliphant and Struhl, Nucl. Acids Res., 16:7673–7683 (1988)].

Likewise, functional molecules have been identified in chemically synthesized random RNA sequence libraries. Affinity selection on dye columns of a library of 100-base, random RNA sequences has shown that approximately one in $10^{10}$ such molecules can specifically bind a small ligand [Ellington and Szostak, Nature, 346:818–822 (1990)]. A random RNA sequence library has also been used to identify 8-base stretches which are recognized by T4 DNA polymerase [Tuerk and Gold, Science, 249:386–390 (1990)].

Fusion-phage systems have also been used to clone and express short, random sequence polypeptides as fusions with a phage coat protein [See Scott and Smith, Science, 249:386–390 (1990); Cwirla, et al., Proc. Natl. Acad. Sci., 87:6378–6382 (1990); Parmley and Smith, Gene, 73:305 (1988)]. Scott and Smith described construction of a library of approximately $4\times10^7$ different hexapeptide epitopes. The library was then screened to identify hexapeptides capable of binding to specific monoclonal antibodies. Likewise, Cwirla, et al., reported that randomly generated peptide sequences are a rich source of ligands. A library of $3\times10^8$ recombinants encoding millions of N-terminal hexapeptide sequences was constructed and then screened with a monoclonal antibody specific for the Tyr-Gly-Gly-Phe sequence present in β-endorphin.

Peptides have also been identified which bind to streptavidin, a protein with no previously known affinity for peptides [Devlin, et al., Science, 249:404–406 (1990)]. Devlin et al. described nine different streptavidin-binding peptide sequences selected from a library of random peptide sequences. The method involved production of a library of sequences by cloning synthetic DNA into E. coli expression vectors. The random sequences were then expressed in a filamentous phage system.

The random sequences and libraries of random sequences described above were produced using various techniques. For example, random sequences were produced by chemical mutagenesis or site-specific mutagenesis of segments of genomic DNA. Also, repeated cycles of solid-phase peptide synthesis were used to produce populations of amino acid sequences [See Geysen, et al., Proc. Natl. Acad. Sci., 81:3998–4002 (1984)].

Alternatively, synthetic random sequences have been produced by mixing together nucleotide precursors in random, undetermined quantities. Further, synthetic random sequences have been produced by mixing together nucleotide precursors in equimolar quantities prior to oligonucleotide or polynucleotide synthesis.

These prior methods for producing random sequences and libraries of sequences are generally inadequate, however. In particular, these methods typically have not designed or synthesized the sequences or libraries to contain particular nucleotide or amino acid compositions or to possess particular biological or chemical characteristics.

For instance, methods for producing sequences using equimolar proportions of nucleotides typically result in amino acid sequences of relatively short length. Only about 9% of the polypeptides translated from DNA encoded by equimolar proportions of nucleotides will reach 50 residues in length. The shortened length of these polypeptides is primarily due to the presence of stop codons in the DNA sequence.

It is known in the art that nucleotides, and groups of nucleotides, in a gene sequence often have various functions in the reading frame of the gene. For example, there may be nucleotides having a regulatory function such as a promoter or start signal. Other nucleotides function in stopping transcription or translation. These nucleotide triplets or "codons" are typically referred to as termination or "stop" codons and generally consist of the nucleotides TAA, TGA, and TAG. In a DNA sequence synthesized from equimolar proportions of nucleotides, about three out of the sixty-four codons (4.7%) are stop codons.

Mandecki has described a method for generating a large pool of semi-random open reading frames ("ORFs") (200–900 residues) [Mandecki, Protein Engineering, 3:221–226 (1990)]. In particular, Mandecki described a method for constructing random DNA sequences using equimolar proportions of nucleotides. The DNA was designed to contain no stop codons by eliminating certain nucleotides in the third position of each codon. The DNA sequence design, however, failed to code for 2 of the 20 common amino acids and for 112 of the 400 possible amino acid pairs. Thus, although Mandecki's design of the sequences eliminated the presence of stop codons, the overall diversity of the sequences was limited. Furthermore, the sequences were cloned in an expression system which produced insufficient product to allow for its isolation.

Scott and Smith, [supra,] also described use of equimolar proportions of nucleotides in producing random oligonucleotide sequences. Specifically, the sequences were synthesized using oligonucleotides with a three residue repeating pattern of $(NNK)_6$, where N is a mixture of all four nucleotides and K is an equimolar mixture of T and G.

Likewise, Devlin et al., [supra,] produced random 15-residue peptide sequences using a three residue repeating pattern. The frequency of termination codons and variation in the number of codons for each amino acid residue was reduced by using $(NNS)_{15}$ to encode 15 random residues where N is a mixture of G, A, T, and C, and S is a mixture of G and C.

Although the methods described by Mandecki, Scott and Smith, and Devlin et al. resulted in gene sequences having greater length, the restrictions imposed on the addition of nucleotides reduced the diversity of the sequences. Moreover, the gene sequences synthesized from arbitrary or even equimolar quantities of nucleotides do not generally encode for polypeptides having characteristics like those found in functional, naturally-occurring proteins.

The nucleocide composition of such synthesized nucleotide sequences may also affect the cloning of the sequences into vectors or other expression systems, particularly with respect to cloning junctions. Cloning junctions in DNA sequences are constant regions of a determined nucleotide sequence which serve as primers and restriction enzyme recognition sites. Such constant regions not only have the affect of potentially limiting the diversity of the gene sequences cloned in a vector but may also adversely affect the secondary structure of the peptide or polypeptide encoded by the gene sequence [See Kolaskar, et al., *Int. J. Peptide Protein Res.*, 22:83–91 (1983); Vonderviszt, et al., *Int. J. Peptide Protein Res.*, 27:483–492 (1986)].

Methods for synthesizing nucleotide sequences and libraries of sequences in the past have typically not addressed the problems associated with cloning junctions. For example, the random sequences described by Mandecki, [supra], had a high frequency of glycine in the cloning junctions, an amino acid which avoids both alpha helix and beta sheet in natural proteins. A repeating pattern of glycine residues can therefore have a negative impact on folding of the proteins by restricting the allowed patterns of secondary structure.

The nucleotide and amino acid composition of the synthesized sequences also affects the biological and chemical properties of the peptides or polypeptides encoded by the sequences. For example, the amino acid composition of a peptide or polypeptide will determine whether it is hydrophilic or hydrophobic and whether it will have a positive or negative electrical charge.

The properties possessed by typical, naturally-occurring proteins have been studied and statistical analyses of such protein sequences have been conducted. Naturally-occurring proteins have been described to characteristically contain certain amino acid compositions [Klapper, *Biochem. Biophys. Res. Com.*, 78:1018–1024 (1977)]. As an example, the high frequency of N-terminal methionine in bacterial proteins is well-known and is explained by its role as a chain initiator [Waller, *J. Mol. Biol.*, 7:483–496 (1967)]. Accordingly, in producing diverse nucleotide sequences and libraries of such sequences, it is desirable and useful to consider the respective nucleotide and amino acid compositions.

SUMMARY OF THE INVENTION

The present invention provides a method for producing a library of diverse nucleotide sequences, comprising the steps of providing a first constant region comprising a first restriction enzyme site and sequentially coupling nucleotides to the constant region in the 3' to 5' direction to form a coding sequence of desired length, wherein the nucleotides for each coupling step are provided in a mixture of pre-determined proportions of A, T, C, and G based upon a known amino acid profile. A second constant region comprising a second restriction enzyme site is coupled to the coding sequence.

The present invention also provides a method for producing a library of vectors having diverse nucleotide sequences, further comprising the steps of digesting the amplified sequences with a first and second restriction enzyme and introducing the digested sequences into a vector.

The present also provides a method for producing a library of diverse polypeptides, further comprising the step of providing proper conditions for the vector to express the sequences.

The present invention also provides a vector comprising at least a promoter which permits transcription of a synthetic coding sequence, a start codon, and a synthetic coding sequence comprising pre-determined proportions of A, C, T, and G based upon a known amino acid profile and operatively linked to the promoter.

The present invention further provides synthetic DNA encoding constant regions and libraries of diverse nucleotide sequences. In addition, the invention provides amino acid sequences encoding ubiquition-fusion polypeptides.

The methods disclosed by the present invention are advantageous in that libraries of diverse nucleotide sequences and polypeptides of useful lengths, compositions, and quantity may be produced. In particular, the methods described by the present invention reduce the frequency of termination codons in the synthesized nucleotide sequences by controlling the nucleotides in the third position of each codon, thereby increasing the length of polypeptides encoded by the sequences. Also, polypeptides and libraries of polypeptides having amino acid compositions similar to a known amino acid profile, and in particular, the amino acid profile of functional proteins found in nature, may be produced without unduly restricting the diversity of the sequences. Furthermore, the nucleotide sequences may be designed so as to reduce the adverse affects of cloning junctions.

The libraries disclosed by the present invention are useful as sources of biologically or chemically functional molecules, as well as research tools in a variety of applications. In particular, the libraries are useful in studying the relationship between peptide sequences and their respective structure, shape, and folding patterns.

DETAILED DESCRIPTION OF THE PREFERRED EMBODIMENTS

Figure 1:
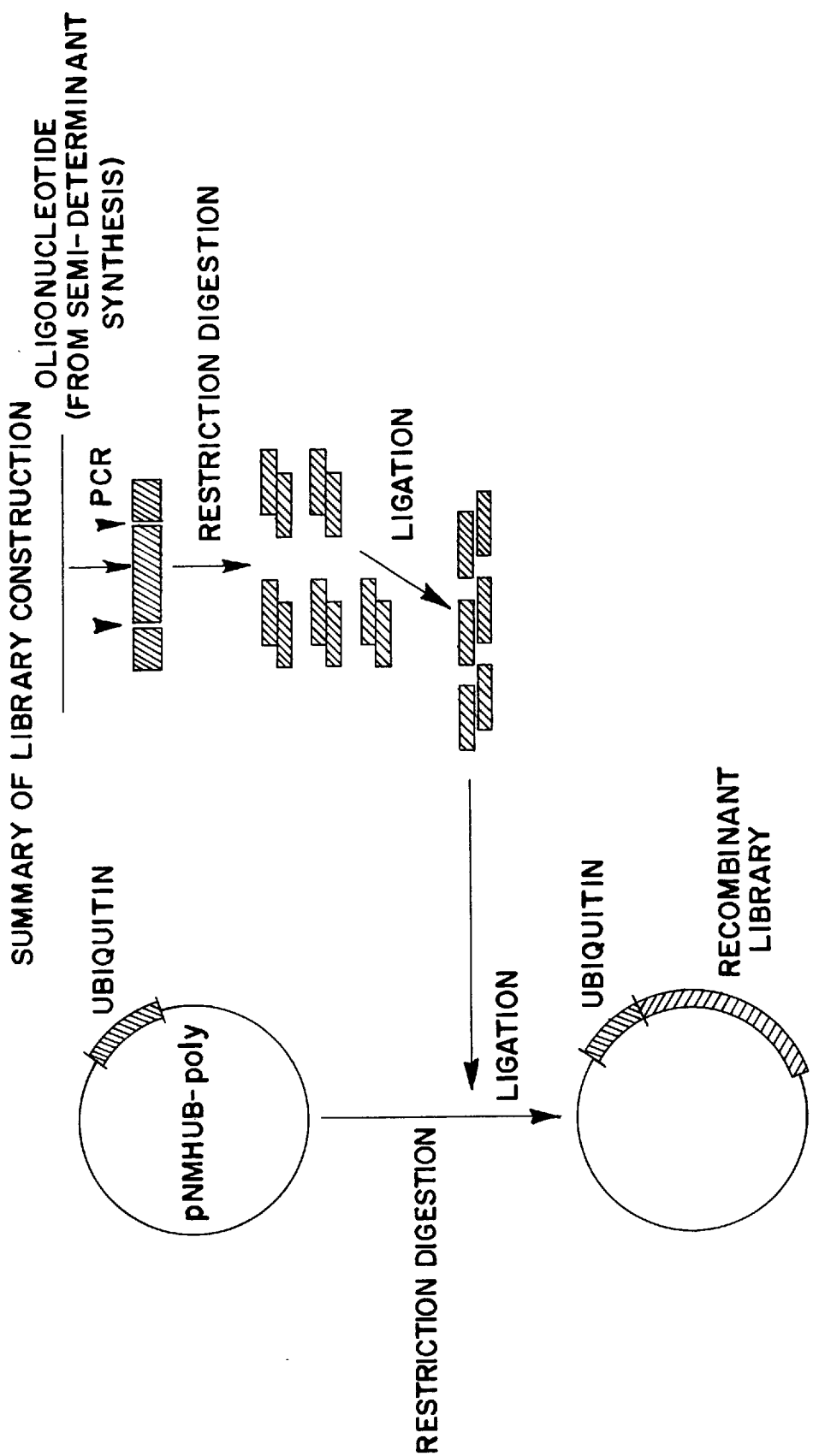
FIG. 1 shows a schematic diagram of one of the methods for constructing a library of diverse nucleotide sequences.

In one embodiment of the present invention, there is provided a method for producing a library of diverse nucleotide sequences. The sequences in the library are designed and synthesized by sequentially coupling nucleotides, wherein the nucleotides for each coupling step are provided in a mixture of pre-determined proportions of A, C, T, and G based upon a known amino acid profile. In a preferred embodiment, the diverse nucleotide sequences encode for the 20 common amino acids in proportions similar to the amino acid proportions found in functional, naturally-occurring proteins. References to "A," "T," "C," and "G" in this specification relate to the nucleotides adenine, thymine, cytosine, and guanine, respectively.

The first step of the method involves providing a polynucleotide sequence comprising a first constant region and a second constant region coupled to a coding sequence that comprises pre-determined proportions of nucleotides. Preferably, a constant region is coupled to both the 5' and the 3' end of the coding sequence. The constant regions can have several functions in the polynucleotide sequence. First, the constant regions serve as primer binding sites for amplification and/or second strand synthesis.

Preferably, the constant region comprises from about 15 to about 25 nucleotide bases. The nucleotide composition of the constant region is also preferably high in C and G content. More preferably, at least 60% of the constant region comprises C and G. As used in this specification and the appended claims, this "%" value represents molar %.

In a preferred embodiment, a constant region is synthesized using standard DNA synthesis techniques known in the art. In synthesizing the constant region, the length and nucleotide composition should be considered. In a more preferred embodiment, the constant region is a sequence identified herein as THL 16, or active variants thereof. Alternatively, the constant region is a sequence identified herein as THL 17, or active variants thereof. In a most preferred embodiment of the invention, the constant region is a sequence identified herein as THL 18, or active variants thereof. Alternatively, the constant region is a sequence identified herein as THL 21 or THL 24, or active variants thereof. "Active variants" are constant regions which have deletions, additions and/or substitutions of nucleotides as compared to the sequence specifically identified, but which are still able to sufficiently hydrogen bond specifically to the desired single strand DNA and act as a foundation for second strand synthesis.

The nucleotide sequences for THL 16, THL 17, THL 18, THL 21, and THL 24 are shown below, as well as in the SEQUENCE LISTING. THL 16:

CGGAATTCCT AGACGT    [seq id no 1]

THL 17:

AGCAGGATCC CTTCGAA    [seq id no 2]

THL 18:

ACGCACTTGC CGAGATCT    [seq id no 3]

THL 21:

CGCGGGTACC TCTACGGATC C    [seq id no 4]

THL 24:

CTTGTCTTAA GACTAAGAGG TGGT    [seq id no 5]

The constant regions also serve as restriction enzyme recognition sites for cloning junctions. The cloning junctions are useful in cloning the synthesized sequence into a vector, as well as for ligating digested sequences together. Because the length of a synthesized polynucleotide sequence is limited by inefficiencies of chemistry, individual nucleotide sequences cannot be made arbitrarily long. Accordingly, it can be useful to construct longer polynucleotide sequences by ligating together segments of DNA that has been digested by certain restriction enzymes.

Accordingly, the constant region also comprises certain nucleotides recognized by a particular restriction enzyme. Preferably, the constant regions comprise restriction enzyme recognition sites for two different restriction enzymes. The constant regions may comprise restriction enzyme recognition sites for two different restriction enzymes that recognize different palindromic sequences but leave compatible cohesive ends. (See Table 2, Example Enzyme Family For Generation Of Compatible Overhangs). Alternatively, the constant regions may comprise restriction enzyme recognition sites for two different restriction enzymes that produce uncompatible overhangs.

Most preferably, the constant regions comprise restriction enzyme recognition sites for restriction enzymes that recognize 4 or 6 base palindromes. Restriction enzymes contemplated by the present invention include, but are not limited to, BamHI (cuts GGATCC), BqlII (cuts AGATCT), and BclI (cuts TGATCA), each leaving a GATC overhang. DNA digested by any member of this family of restriction enzymes can be ligated to DNA digested by itself or by any other member of the family. If a BamHI fragment is ligated to a BqlII fragment, both of those recognition sites is destroyed, but at the same time, a BstYI site is created.

There are also families of restriction enzymes which make compatible sticky ends, including but not limited to, GC, TA, CATG, CCGG, CGCG, CTAG, GGCC, GTAC, TCGA, CATG, and TGCA. For example, a CG overhang is produced by the restriction enzymes MaeII, HpaII, HinPI, and TaqI.

The constant regions may also encode for one or more particular amino acids. Preferably, the constant region codes for an amino acid, or amino acid pairs, which do not restrict possible secondary structural motifs. The constant region also preferably codes for amino acids which are necessarily under-represented in diverse nucleotide sequences designed to minimize stop codons, including but not limited to, glutamate, lysine, tyrosine, cystine, and glutamine. Leucine, glutamine and arginine are found in helix, extended, turn, and coil conformations with almost equal probability and are thus, non-restrictive and most preferable as constant region amino acids.

Next, the coding sequence comprising diverse nucleotide sequences is designed and synthesized. This sequence is synthesized using standard DNA synthesis techniques known in the art. The coding sequence comprises pre-determined proportions of nucleotides, as described further below. In a preferred embodiment, the pre-determined proportions of nucleotides are provided in a three base repeating pattern, as described further in the Examples of the present application. The coding sequence is also preferably designed and synthesized in view of the final purpose of the library, and in particular, the library's gene translation products. The library of diverse nucleotide sequences contemplated by the disclosed methods herein can be used to, among other things, investigate the distribution of globular structures, ligand binding, and enzymatic function.

Prior to synthesis of the coding sequence, the proportions of nucleotides are determined. More particularly, the proportions of nucleotides are determined based upon a known amino acid profile. Preferably, the proportions are determined using the amino acid profile of a known, functional protein, and more preferably, using the amino acid profile of a known, naturally-occurring and functional protein.

In a preferred embodiment of the invention, and as shown in Example 1, in determining the proportions of nucleotides, the probability for each base triplet using given input proportions of the four nucleotides A, T, C, and G, at each of the three positions in a codon, is calculated. Then, the sums of the probabilities for triplets coding for each amino acid and for stop codons is calculated and listed. This list relates to the amino acid composition of the polypeptides encoded by DNA that includes the three residue repeat pattern specified by the given nucleotide composition. Other characteristics of the corresponding gene translation products, such as net charge, and percentages of interior (hydrophobic), exterior (hydrophilic) and ambivalent amino acids, may also be calculated.

All of these calculations may be performed using a computer spreadsheet program. Preferably, these calculations are performed using the commercially available computer program, Lotus® 1, 2, 3®. As shown in Example 1 below, input nucleotide proportions were optimized using the Lotus® 1, 2, 3® program. By determining the proportions of nucleotides in each of the three positions of a codon, the similarities between a known amino acid profile and a synthesized sequence can be optimized, while minimizing the occurrence of stop codons in the synthesized sequences. Determining the nucleotide and amino acid composition of the nucleotide sequences also helps limit the gene sequences' translation products to compositions which biological and chemical systems have used successfully, particularly with respect to folding, subunit association, binding, and catalytic function.

Further, amino acid substitutions in the sequence may be calculated to maintain desirable characteristics. For example, lysine, which has a positively-charged side chain, is often absent or present in reduced quantities in sequences that have been designed and synthesized so as to avoid stop codons. Such absence or reduced quantities of lysine can be partially compensated for by an increase in the presence of arginine, another positively-charged amino acid. Compensatory deviations in amino acid composition are optimized by designing sequences having net charge and content of hydrophobic, hydrophilic, or ambivalent amino acids similar to, for example, those found in naturally-occurring, functional proteins.

In a more preferred embodiment, proportions of nucleotides are provided in a three base repeating pattern, comprising from about 6% to 15% T, from about 18% to 27% C, from about 29% to 36% A, and from about 31% to 41% G in the first position; from about 23% to 29% T, from about 21% to 26% C, from about 20% to 31% A, and from about 21% to 27% G in the second position; and from about 60% to 74% T and/or C, 0% A, and from about 26% to 40% G in the third position. These "%" values represent molar %. A coding sequence comprising these nucleotide proportions encodes for polypeptides containing all 20 amino acids in proportions similar to that found in naturally-occurring biological proteins. Further, these nucleotide proportions represent optimized net charge and percentages of hydrophilic, ambivalent, and hydrophobic amino acids similar to those of natural proteins while minimizing the probability of stop codons.

Nucleotides from mixtures having the pre-determined proportions of A, C, T, and G are then sequentially coupled in a 3' to 5' direction to form a coding sequence of a desired length. DNA synthesis, or nucleotide coupling, techniques are well known in the art, and include but are not limited to, solid phase phosphoramidite chemistry. Alternatively, the sequence may be synthesized in an automated synthesizer.

In a preferred embodiment, a coding sequence comprising a three base repeating pattern is synthesized and is coupled to a first constant region and a second constant region. In a more preferred embodiment, this sequence a 94 base sequence referred to herein as "THL 94". The THL 94 sequence is shown below, as well as in the SEQUENCE LISTING.

---

AGCAG GAT CCC TTC GAA $N_1N_2N_3$ $N_1N_2N_3$ $N_1N_2N_3$ $N_1N_2N_3$    29
    Asp Pro Phe Glu    Xaa      Xaa      Xaa      Xaa
                                     5

$N_1N_2N_3$ $N_1N_2N_3$ $N_1N_2N_3$ $N_1N_2N_3$ $N_1N_2N_3$ $N_1N_2N_3$ $N_1N_2N_3$ $N_1N_2N_3$    53
  Xaa     Xaa     Xaa     Xaa     Xaa     Xaa     Xaa     Xaa
               10                                 15

$N_1N_2N_3$ $N_1N_2N_3$ $N_1N_2N_3$ $N_1N_2N_3$ $N_1N_2N_3$ $N_1N_2N_3$ $N_1N_2N_3$    77
  Xaa     Xaa     Xaa     Xaa     Xaa     Xaa     Xaa
                      20

$N_2AC$ GTC TAGGAATTCC G    94
  Xaa Val
     25

---

WHEREIN $N_1$=8% T, 21% C, 32% A, 39% G;

$N_2$=28% T, 25% C, 22% A, 25% G; and $N_3$=30% T, 30% C, 0% A, 40% G. (seq id no 6)

For purposes of the SEQUENCE LISTING of the present application, nucleotide "N" refers to either $N_1$, $N_2$, or $N_3$, as provided by the specification of the present application and does not refer to an unknown nucleotide.

Further, amino acid "Xaa" in the SEQUENCE LISTING of the present application refers to amino acids as provided by the specification of the present application and does not refer to an unknown amino acid.

The amino acid composition for the diverse nucleotide sequences encoded by THL 94 DNA is shown in Example 1. The number of possible nucleotide sequences produced in THL 94 synthesis is $1.7 \times 10^{34}$, and the number of possible amino acid sequences encoded is $4 \times 10^{26}$.

In a most preferred embodiment, the sequence is a 132 base sequence referred to herein as "THL 132". The THL 132 sequence is shown below, as well as in the SEQUENCE LISTING.

| ACGCACTTGC | CGA | GAT | CTN$_2$ | N$_1$N$_2$N$_3$ | N$_1$N$_2$N$_3$ | N$_1$N$_2$N$_3$ | N$_1$N$_2$N$_3$ | N$_1$N$_2$N$_3$ | 34 |
|---|---|---|---|---|---|---|---|---|---|
| | Asp | Leu | Xaa | Xaa | Xaa | Xaa | Xaa | | |
| | | | | | 5 | | | | |
| N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | | 58 |
| Xaa | Xaa | Xaa | Xaa | Xaa | Xaa | Xaa | Xaa | | |
| | | 10 | | | | | 15 | | |
| N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | | 82 |
| Xaa | Xaa | Xaa | Xaa | Xaa | Xaa | Xaa | Xaa | | |
| | | | | 20 | | | | | |
| N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | | 106 |
| Xaa | Xaa | Xaa | Xaa | Xaa | Xaa | Xaa | Xaa | | |
| | 25 | | | | | 30 | | | |
| N$_1$N$_2$N$_3$ | N$_2$N$_3$G | GAT | CCG | TAGAGGTACC | CGCG | | | | 132 |
| Xaa | Xaa | Asp | Pro | | | | | | |
| | | 35 | | | | | | | |

WHEREIN

N$_1$=8% T, 21% C, 32% A, 39% G;

N$_2$=28% T, 25% C, 22% A, 25% G; and

N$_3$=30% T, 30% C, 30% A, 40% G. [seq id no 7]

Alternatively, the sequence is a 152 base sequence referred to herein as "THL 152". The THL 152 sequence is shown below, as well as in the SEQUENCE LISTING.

| CTTGTCTTAA | GACTAAGAGG | TGGT | N$_1$N$_2$N$_3$ | N$_1$N$_2$N$_3$ | N$_1$N$_2$N$_3$ | N$_1$N$_2$N$_3$ | | 36 |
|---|---|---|---|---|---|---|---|---|
| | | | Xaa | Xaa | Xaa | Xaa | | |
| N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | 60 |
| Xaa | Xaa | Xaa | Xaa | Xaa | Xaa | Xaa | Xaa | |
| 5 | | | | | 10 | | | |
| N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | 84 |
| Xaa | Xaa | Xaa | Xaa | Xaa | Xaa | Xaa | Xaa | |
| | | 15 | | | | | 20 | |
| N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | 108 |
| Xaa | Xaa | Xaa | Xaa | Xaa | Xaa | Xaa | Xaa | |
| | | | | 25 | | | | |
| N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_1$N$_2$N$_3$ | N$_2$N$_3$G | 132 |
| Xaa | Xaa | Xaa | Xaa | Xaa | Xaa | Xaa | Xaa | |
| | | 30 | | | | | 35 | |
| GAT | CCG | TAGAGGTACC | CGCG | | | | | 152 |
| Asp | Pro | | | | | | | |

WHEREIN

N$_1$=8% T, 21% C, 32% A, 39% G;

N$_2$=28% T, 25% C, 22% A, 25% G; and

N$_3$=30% T, 30% C, 0% A, 40% G. [seq id no 8]

Following synthesis, the sequences may be purified using various methods known in the art. Preferably, constant region sequences are purified on columns containing DNA grade Sephadex® using standard equilibration and elution buffers known in the art. More preferably, constant region sequences are purified on commercially available disposable Sephadex® G-25 columns (Nap-100®, Pharmacia®).

The coding sequences may also be purified by standard DNA purification techniques known in the art. More preferably, the coding sequences are purified on oligonucleotide purification cartridges ("OPC") commercially available from Applied Biosystems®, Foster City, Calif.

Preferably, the sequences are then amplified. More preferably, the sequences are amplified using polymerase chain reaction ("PCR") techniques known in the art [See generally, U.S. Pat. No. 4,683,202, issued Jul. 28, 1987, incorporated herein by reference]. The PCR amplification of the sequences is believed to assist in maintaining the sequence library diversity. It is further believed that obtaining multiple copies of each sequence prior to the cloning step in a method of the present invention assures that a larger proportion of starting sequences will reach the final library.

Preferably, PCR amplification is performed using a GeneAmp® PCR Reagent Kit (commercially available from Perkin-Elmer® Corporation, Norwalk, Conn.) and a DNA Thermal Cycler (commercially available from Perkin-Elmer® Corporation, Norwalk, Conn.). Alternatively, second strand synthesis may be performed using the Klenow fragment of DNA polymerase.

The present invention also provides a method for producing a library of vectors with diverse nucleotide sequences. The method comprises the steps described above, and further comprises the step of digesting with restriction enzyme.

In a more preferred embodiment, the sequences are amplified prior to digestion with restriction enzyme.

Preferably, the sequences are digested with restriction enzyme under reaction conditions sufficient to allow complete digestion of the sequences. More particularly, the sequences are digested with restriction enzymes having recognition sites in the constant regions, as described above and in Table 2. The restriction enzymes contemplated by the present invention are commercially available from vendors including, but not limited to, New England BioLabs, Boehringer Mannheim Chemical Company, and Promega.

Preferably, the amplified sequences are digested with two different restriction enzymes. More preferably, the sequences are digested with two different restriction enzymes that produce non-compatible overhangs. It is believed that production of non-compatible overhangs assists in preserving orientation of the sequences when introduced into a vector.

The digested sequences are then introduced into a vector comprising at least a promoter and an initiation or start codon. The start codon is typically the codon, ATG. The term vector as used herein is used in its broadest sense, and includes but is not limited to, expression vectors, naturally-occurring plasmids, bacteria, and phage. Numerous types of vectors are commercially available or available from public cell repositories such as the American Type Culture Collection (ATCC). The sequences are preferably introduced into the vector using standard cloning techniques known in the art [Maniatis, et al. *Molecular Cloning: A Laboratory Manual*, Cold Spring Harbor (1982)]. The vector is preferably treated with the same restriction enzymes used to digest the sequences prior to the cloning step. The vector is also preferably treated with phosphatase. In a more preferred embodiment, the vector is treated with calf intestine alkaline phosphatase (commercially available from Promega).

Alternatively, the digested sequences may be ligated together prior to cloning, preferably using T4 DNA ligase (Promega) or a Takara ligation kit (Takara Biochemicals). The digested sequences may also be ligated together using any commercially available DNA ligase. The sequences may be ligated together to preserve the orientation and identity of the coding strand. The importance of reading from a predetermined coding strand lies in the relative ease with which a desired output, or amino acid composition, can be engineered in a single strand system. The length of the sequence fragments can be controlled by adjusting the ligation conditions or by performing a partial digest with a restriction enzyme. Also, a stop codon can be added to the polynucleotide sequence by ligating a linker containing sites to the large fragments in order to facilitate cloning the polynucleotide sequence into a vector.

The promoter in the vector functions in binding an RNA polymerase that begins transcription of m RNA. The promoter may be any sequence of any given length that is capable of initiating transcription of the synthetic coding sequence. The promoter should be compatible with the vector, however, so as to provide transcription and translation of the sequences. More preferably, the promoter is an inducible promoter. It will be apparent to those skilled in the art that certain features of a particular promoter may be useful in a given vector. In a preferred embodiment of the invention, the promoter is functional in a fusion-protein vector. In a more preferred embodiment, the promoter is functional in a ubiquitin-fusion vector. In a most preferred embodiment, the promoter is functional in the ubiquitin-fusion vector, pNMHUBpoly.

Preferably, the sequence is introduced into a vector comprising a relatively simple cloning system with a high yield of recombinants and a high rate of protein expression. In a more preferred embodiment, the sequence is introduced into a fusion-protein vector. A fusion-protein vector is particularly useful so that each polypeptide translated from the library of diverse nucleotide sequences contains a constant protein region to act as a marker for analysis and purification. A fusion-protein vector which includes a specific protease cleavage site at the C-terminus of the constant region is even more preferable.

Figure 2:
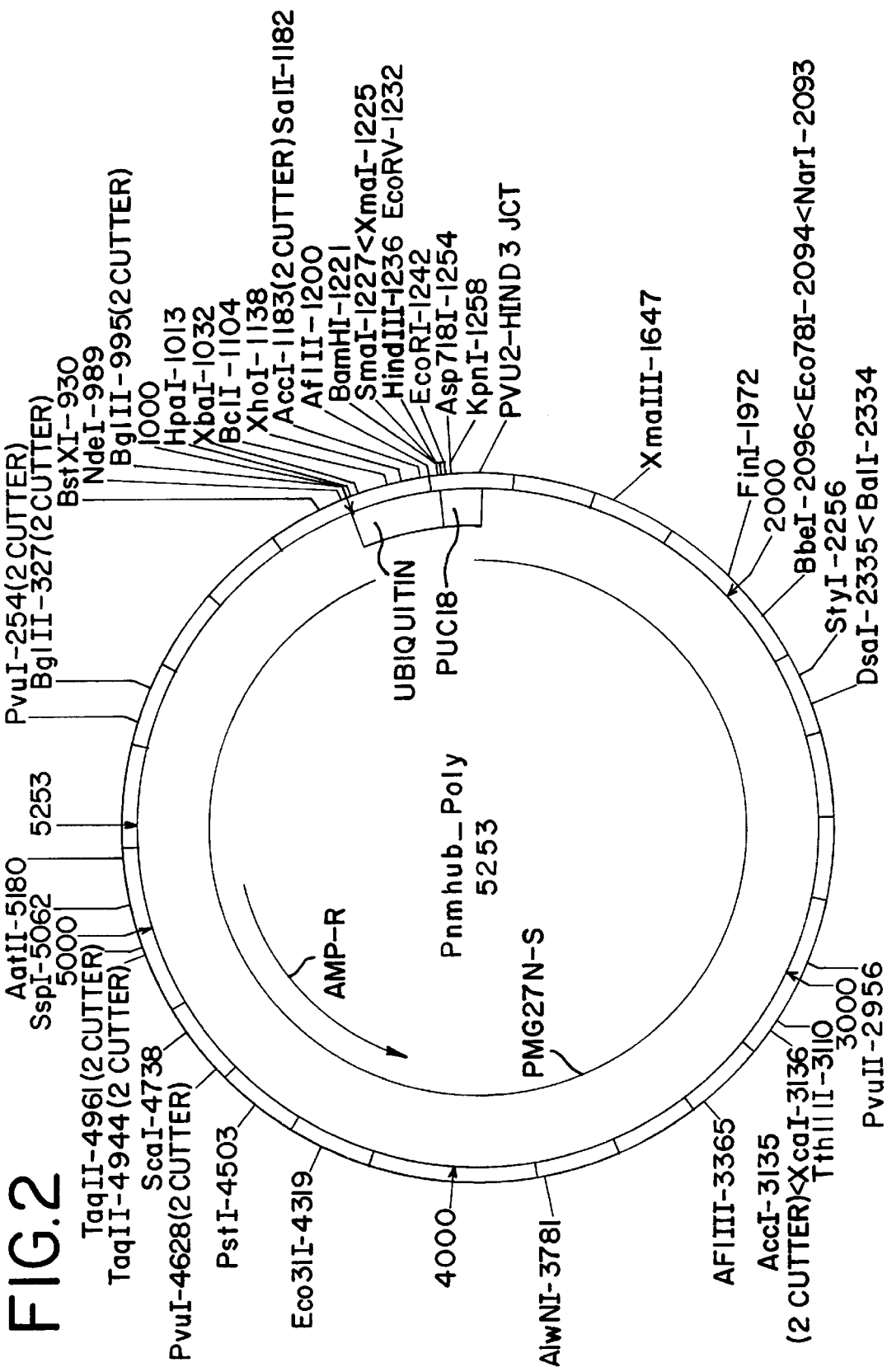
FIG. 2 shows a restriction map of the pNMHUBpoly vector.

In a most preferred embodiment, the sequence is introduced into the ubiquitin-fusion vector, pNMHUBpoly. A schematic diagram of this method is shown in FIG. 1. The pNMHUBpoly vector comprises the lambda $P_L$ promoter, a cII ribosome binding site, the human ubiquitin gene, and a multiple cloning site. The pNMHUBpoly vector is available from Dr. Tauseef Butt, SmithKline-Beecham Corp., Philadelphia, Pa. The restriction map of pNMHUBpoly is shown in FIG. 2. [See also, Ecker, et al., *J. Biol. Chem.*, 262:14213–14221 (1987)].

The $P_L$ promoter in pNMHUBpoly tightly controls transcription so that gene products are not produced until it is induced, thereby reducing the possibility of toxicity of the polypeptides encoded by the library. When this expression system is induced, large quantities of polypeptides are produced. Although not fully understood, it is believed that fusion with the ubiquitin protein assists in solubilizing the gene products, and may even assist in folding of the extension polypeptides.

The present invention further provides a method for producing a library of polypeptides, wherein the vector described above is provided proper conditions so as to express the diverse nucleotide sequences. The polypeptides are expressed and then may be purified. In a preferred embodiment, the vector comprising the library of diverse nucleotide sequences is introduced into *E. coli* by standard cell transformation techniques known in the art. In a more preferred embodiment, a protein-fusion vector comprising the library is introduced into *E. coli*.

In a most preferred embodiment, the pNMHUBpoly vector comprising the library is introduced into *E. coli*, and preferably, *E. coli* strains MM294 or AR68. Both *E. coli* strains MM294 and AR68 are publicly available from ATTC. MM294 Cl+ has a wild type repressor protein and is useful in amplification and construction. AR68 has a temperature sensitive Cl repressor protein and is useful in vector expression.

When cloned into pNMHUBpoly, dsTHL 94 provides gene libraries encoding ubiquitin fusion proteins having the amino acid sequence shown below, as well as in the SEQUENCE LISTING.

| Met | Gln | Ile | Phe | Val | Lys | Thr | Leu | Thr | Gly | Lys | Thr | Ile | Thr |
|-----|-----|-----|-----|-----|-----|-----|-----|-----|-----|-----|-----|-----|-----|
|     |     |     |     | 5   |     |     |     |     | 10  |     |     |     |     |
| Leu | Glu | Val | Glu | Pro | Ser | Asp | Thr | Ile | Glu | Asn | Val | Lys | Ala |
| 15  |     |     |     |     | 20  |     |     |     |     | 25  |     |     |     |
| Lys | Ile | Gln | Asp | Lys | Glu | Gly | Ile | Pro | Pro | Asp | Gln | Gln | Arg |

| Leu | Ile   30 | Phe   45 | Ala | Gly | Lys | Gln   35 | Leu | Glu | Asp | Gly | Arg   40 | Thr   55 | Leu |
|-----|----------|----------|-----|-----|-----|----------|-----|-----|-----|-----|----------|----------|-----|
| Ser | Asp | Tyr | Asn   60 | Ile | Gln | Lys | Glu | Ser   65 | Thr | Leu | His | Leu | Val   70 |
| Leu | Arg | Leu | Arg | Gly   75 | Gly | Ala | Asp | Pro | Phe   80 | Glu | Xaa | Xaa | Xaa |
| Xaa   85 | Xaa | Xaa | Xaa | Xaa | Xaa   90 | Xaa | Xaa | Xaa | Xaa | Xaa   95 | Xaa | Xaa | Xaa |
| Xaa | Xaa   100 | Xaa | Xaa$_1$ | Val | | | | | | | | | |

WHEREIN

Xaa$_1$=Tyr, His, Asn, or Asp [seq id no 9]

When cloned into pNMHUBpoly, dsTHL 152 provides gene libraries encoding ubiquitin fusion proteins having the following amino acid sequence:

| Met | Gln | Ile | Phe | Val   5 | Lys | Thr | Leu | Thr | Gly   10 | Lys | Thr | Ile | Thr |
|-----|-----|-----|-----|---------|-----|-----|-----|-----|----------|-----|-----|-----|-----|
| Leu   15 | Glu | Val | Glu | Pro | Ser   20 | Asp | Thr | Ile | Glu | Asn   25 | Val | Lys | Ala |
| Lys | Ile   30 | Gln | Asp | Lys | Glu | Gly   35 | Ile | Pro | Pro | Asp | Gln   40 | Gln | Arg |
| Leu | Ile | Phe   45 | Ala | Gly | Lys | Gln | Leu   50 | Glu | Asp | Gly | Arg | Thr   55 | Leu |
| Ser | Asp | Tyr | Asn   60 | Ile | Gln | Lys | Glu | Ser   65 | Thr | Leu | His | Leu | Val   70 |
| Leu | Arg | Leu | Arg | Gly   75 | Gly | Xaa | Xaa | Xaa | Xaa   80 | Xaa | Xaa | Xaa | Xaa |
| Xaa   85 | Xaa | Xaa | Xaa | Xaa | Xaa   90 | Xaa | Xaa | Xaa | Xaa | Xaa   95 | Xaa | Xaa | Xaa |
| Xaa | Xaa   100 | Xaa | Xaa | Xaa | Xaa | Xaa   105 | Xaa | Xaa | Xaa | Xaa | Xaa   110 | Xaa | Xaa |
| Asp | Pro | | | | | | | | | | | | |

[seq id no 10]

These libraries, designated herein as LIB38 DNA, encode an additional 38 amino acids fused to ubiquitin.

When dsTHL 132 is cloned into LIB38 DNA, 71 amino acid additions are produced, and ubiquitin fusion polypeptides having the following amino acid sequence are produced.

Polypeptides expressed by the library of diverse nucleotide sequences may then be cleaved from the carboxyl terminus of ubiquitin by processing with commercially available rabbit reticulocyte lysate. The polypeptides translated from the library may also be cleaved by processing with ubiquitin hydrolase. Purification may be performed by ubiquitin-fusion purification or affinity chromatography and fusion cleavage.

The library of polypeptides may then be evaluated or screened, singularly or in pools, to determine desired

| Met | Gln | Ile | Phe | Val   5 | Lys | Thr | Leu | Thr | Gly   10 | Lys | Thr | Ile | Thr |
|-----|-----|-----|-----|---------|-----|-----|-----|-----|----------|-----|-----|-----|-----|
| Leu   15 | Glu | Val | Glu | Pro | Ser   20 | Asp | Thr | Ile | Glu | Asn   25 | Val | Lys | Ala |
| Lys | Ile   30 | Gln | Asp | Lys | Glu | Gly   35 | Ile | Pro | Pro | Asp | Gln   40 | Gln | Arg |
| Leu | Ile | Phe   45 | Ala | Gly | Lys | Gln | Leu   50 | Glu | Asp | Gly | Arg | Thr   55 | Leu |
| Ser | Asp | Tyr | Asn   60 | Ile | Gln | Lys | Glu | Ser   65 | Thr | Leu | His | Leu | Val   70 |
| Leu | Arg | Leu | Arg | Gly   75 | Gly | Xaa | Xaa | Xaa | Xaa   80 | Xaa | Xaa | Xaa | Xaa |
| Xaa   85 | Xaa | Xaa | Xaa | Xaa | Xaa   90 | Xaa | Xaa | Xaa | Xaa | Xaa   95 | Xaa | Xaa | Xaa |
| Xaa | Xaa   100 | Xaa | Xaa | Xaa | Xaa | Xaa   105 | Xaa | Xaa | Xaa | Xaa | Xaa   110 | Xaa | Xaa |
| Asp | Leu | Xaa   115 | Xaa | Xaa | Xaa | Xaa | Xaa   120 | Xaa | Xaa | Xaa | Xaa | Xaa   125 | Xaa |
| Xaa | Xaa | Xaa | Xaa   130 | Xaa | Xaa | Xaa | Xaa | Xaa   135 | Xaa | Xaa | Xaa | Xaa | Xaa   140 |
| Xaa | Xaa | Xaa | Xaa | Xaa   145 | Asp | Pro | | | | | | | |

[seq id no 11]

structural, chemical, or biological functions. Evaluation of the polypeptides may include gene sequencing and/or amino acid analysis.

The present invention also provides a vector comprising at least a promoter which permits transcription of a synthetic coding sequence, a start codon and a synthetic coding sequence comprising pre-determined proportions of A, C, T, and G based upon a known amino acid profile and operatively linked to the promoter.

In a preferred embodiment, the vector is a fusion-protein vector. In a more preferred embodiment, the vector is a ubiquitin-fusion vector. In a most preferred embodiment, the ubiquitin-fusion vector is pNMHUBpoly.

The present invention also provides synthetic DNA and amino acid sequences as described above and further provided in the SEQUENCE LISTING of the present application.

EXAMPLES

The methods described below were performed according to standard techniques known in the art, and as described by Maniatis, et al., *Molecular Cloning: A Laboratory Manual*, Cold Spring Harbor (1982), unless indicated otherwise. Materials purchased from commercial vendors were used according to manufacturer's instructions, unless indicated otherwise.

Example 1

Using Lotus® 1, 2, 3®, input nucleotide proportions were determined using the amino acid profile described by Klapper, *Biochem. Biophys. Res. Com.*, 78: 1018–1024 (1977). The coding sequence was designed using a repeating pattern of nucleotide mixtures designated "$N_1$ $N_2$ $N_3$."

In Table 1 below, Column 1 lists the twenty common amino acids. Column 2 identifies a targeted or "desired" amino acid composition. Column 3, XXX, represents the amino acid composition of synthesized DNA which has been completely randomized at each residue by adding equimolar quantities of T, C, A, and G during synthesis. Column 4 identifies the amino acid profile of the designed coding sequence wherein $N_1$=8% T, 21% C, 32% A, 39% G; $N_2$=28% T, 25% C, 22% A, 25% G; $N_3$=30% T, 30% C, 0% A, 40% G. STOP refers to the frequency of stop codons in the synthesized sequence. Chrg refers to net charge which equals Asp+Glu+His-Lys-Arg. Ext refers to exterior amino acids which equals Asp+Glu+His+Lys+Asn+Gln+Arg. Int refers to interior amino acids which equals Phe+Ile+Leu+Met+Val. Amb refers to ambivalent amino acids which equals =Ala+Cys+Gly+Pro+Ser+Thr+Trp+Tyr.

TABLE 1

| 1 | 2<br>Desired | 3<br>XXX | 4<br>$N_1N_2N_3$ |
|---|---|---|---|
| Ala | 9.2 | 6.2 | 9.8 |
| Cys | 2.8 | 3.1 | 1.2 |
| Asp | 5.5 | 3.1 | 5.1 |
| Glu | 6.2 | 3.1 | 3.4 |
| Phe | 3.5 | 3.1 | 1.3 |
| Gly | 7.8 | 6.2 | 9.8 |
| His | 2.0 | 3.1 | 2.8 |
| Ile | 4.6 | 4.7 | 5.4 |
| Lys | 7.0 | 3.1 | 2.8 |
| Leu | 7.5 | 9.4 | 6.8 |
| Met | 1.7 | 1.6 | 3.6 |
| Asn | 4.4 | 3.1 | 4.2 |
| Pro | 4.6 | 6.2 | 5.2 |

TABLE 1-continued

| 1 | 2<br>Desired | 3<br>XXX | 4<br>$N_1N_2N_3$ |
|---|---|---|---|
| Gln | 3.9 | 3.1 | 1.8 |
| Arg | 4.7 | 9.4 | 8.5 |
| Ser | 7.1 | 9.4 | 6.8 |
| Thr | 6.0 | 6.2 | 8.0 |
| Val | 6.9 | 6.2 | 10.9 |
| Trp | 1.1 | 1.6 | 0.8 |
| Tyr | 3.5 | 3.1 | 1.1 |
| STOP | 0 | 4.7 | 0.7 |
| Chrg | 2 | 6.2 | 0.1 |
| Ext | 34 | 30 | 29 |
| Amb | 42 | 44 | 43 |
| Int | 24 | 26 | 28 |

Example 2

A 94 base sequence, referred to herein as THL 94, was designed and synthesized as described below. More particularly, THL 94 comprises 60 residues of nucleotide bases arranged in a three base repeating pattern, the reading frame of which codes for all 20 amino acids with only a 0.7% probability of stop codons.

The sequence of THL 94 is shown below, as well as in the SEQUENCE LISTING.

```
AGCAG GAT CCC TTC GAA N1N2N3 N1N2N3 N1N2N3 N1N2N3          29
      Asp Pro Phe Glu  Xaa    Xaa    Xaa    Xaa
                               5

N1N2N3 N1N2N3 N1N2N3 N1N2N3 N1N2N3 N1N2N3 N1N2N3 N1N2N3    53
 Xaa    Xaa    Xaa    Xaa    Xaa    Xaa    Xaa    Xaa
               10                                  15

N1N2N3 N1N2N3 N1N2N3 N1N2N3 N1N2N3 N1N2N3 N1N2N3           77
 Xaa    Xaa    Xaa    Xaa    Xaa    Xaa    Xaa
                       20

N2AC GTC TAGGAATTCC G                                      94
 Xaa Val
  25
```

WHEREIN $N_1$=8% T. 21% C, 32% A, 39% G;

$N_2$=28% T, 25% C, 22% A, 25% G; and $N_3$=30% T, 30% C, 0% A, 40% G.

The corresponding amino acid composition for THL 94 DNA is shown in Example 1, Table 1, Column 4.

A. DNA Synthesis and Purification

The constant regions and coding sequence identified above were synthesized by solid-phase phosphoramidite chemistry on an Applied Biosystems® 380B DNA Synthesizer. The constant regions, THL 16 and THL 17, were synthesized by the Trityl-off procedure.

After synthesis, the constant region sequences were cleaved and dissolved in ammonium hydroxide (Mallinckrodt Chemicals). Next, the sequences were evaporated to dryness in a Savant SpeedVac Concentrator, and dissolved in 500 μl TE buffer (10 mM Tris, 1 mM EDTA, pH 8.0).

The constant region sequences were then purified on disposable Sephadex® G-25 columns (NAP-10®, purchased from Pharmacia®) using TE buffer. DNA concentrations (μg/μl) were calculated by determining the spectrophotometric absorbance at 260 nm (using a Beckman DU-70 Spectrophotometer) and multiplying the value obtained by 0.033.

THL 94 DNA was synthesized using the Trityl-on method with 0.2 μM columns and 100 mM cyanoethyl phosphoramidites (purchased from Applied Biosystems®) in anhydrous acetonitrile (purchased from Baker Chemicals). Phosphoramidite solutions were premixed in three bottles in the nucleotide proportions identified in Example 1 for $N_1$, $N_2$, and $N_3$. The overall yield of synthesis was 38.96, calculated from the trityl released on the first and last steps of synthesis. The trityl concentration was measured as the absorption at 498 nm in acetonitrile containing 0.1M toluene sulfonic acid.

THL 94 was then purified using syringe cartridges purchased from Applied Biosystems®. Two or three cartridges were attached in series to increase the purification yield.

B. Polymerase Chain Reaction and dsDNA Purification

The synthesized sequences were then amplified using polymerase chain reaction techniques known in the art [See generally, *PCR Technology: Principles and Applications for DNA Amplification*, Erlich, Ed., Stockton Press, 1989]. PCR amplification was carried out in 100 μl aliquots using a GeneAmp® PCR Reagent Kit and a DNA Thermal Cycler (both purchased from Perkin Elmer® Corporation, Norwalk, Conn.). Each aliquot contained 200 ng of template, 250 ng of each primer, 200 μM of each of the four dNTPs, 2.5 U Taq polymerase in GeneAmp® buffer, along with additional 3 mM $MgCl_2$. To each tube, 60 μl mineral oil (Sigma Chemicals, St. Louis, Mo.) was added to eliminate evaporation and reflux. The reactions were cycled through either 5 or 6 rounds of denaturation (at 94° C., 20 seconds), annealing (at 41° C., 20 seconds) and extension (at 60° C., 20 seconds). The double-stranded PCR product is referred to as dsTHL 94.

Following PCR amplification, the oil was pipetted off, and the 10 tubes were pooled. The amplified sequences were extracted with chloroform (purchased from Mallinkrodt Chemicals) to remove the last traces of mineral oil, and passed over a disposable Sephadex® G-25 column (NAP-10®, purchased from Pharmacia®) to separate the synthesized DNA sequences from the mononucleotides. Ethanol precipitations were carried out by adding 0.1 volume of 3M potassium acetate and 2 volumes absolute ethanol, vortexing briefly, and cooling at −40° C. for 10 minutes. The mixture was then spun at 40° C. for 10 minutes in a microfuge. The liquid was decanted, and the pellet was washed with 70% ethanol. After the wash was removed, the pellet was dried in a SpeedVac for 30–60 minutes. The purification procedure yielded 546 μg DNA corresponding to a library diversity of about $10^{16}$. The purified PCR product was then stored dry at 4° C. until use.

C. Restriction Enzyme Digestion

The products of the PCR amplification were then tested with restriction enzymes to confirm the presence of restriction sites in the constant regions of the sequence. Restriction enzyme MaeII (purchased from Boehringer Manheim Biochemicals, Indianapolis, Ind.) digestions were carried out in buffer H (50 mM Tris-HCl, 10 mM $MgCl_2$, 100 mM NaCl, 1 mM dithioerythriol, pH 7.5) at 50° C. overnight. It was found that under these conditions, MaeII also dephosphorylated the DNA fragments. Accordingly, when required, the fragments were rephosphorylated with T4 Polynucleotide Kinase (purchased from Promega) in 50 mM Tris-HCl, pH 7.5, 10 mM $MgCl_2$, 5 mM dithiotreitol, 1 mM ATP, 50 μg/ml bovine serum albumin ("BSA"), prior to ligation.

Restriction enzyme BstBI (New England Biolabs, Beverly, Me.) digests were performed in NE Buffer 4 (20 mM Tris-acetate, 10 mM magnesium acetate, 50 mM potassium acetate, 1 mM DTT, pH 7.9) at 65° C. overnight.

Restriction enzyme BamHI and EcoRI (Promega) as well as HindIII (Boehringer Manheim Biochemicals), digests are carried out in buffer B (10 mM Tris-HCl, 5 mM $MgCl_2$, 100 mM NaCl, 1 mM 2-mercaptoethanol, pH 8.0) at 37° C. for at least 4 hours and usually overnight.

D. Ligation of Fragments

Ligation of the digested sequences was performed in 40 mM Tris-HCl, pH 7.5, 10 mM $MgCl_2$, 10 mM DTT containing 1 mM ATP and T4 DNA ligase (purchased from Promega). Typically, overnight ligations were incubated at 16° C., except that MaeII fragments were incubated at 4° C.

E. DNA Fragment Purification

DNA fragments were gel purified using Ultra-pure Electrophoresis Grade Agarose (purchased from Bethesda Research Laboratories, Gaithersburg, Md.) and a Horizon 58 gel apparatus (Bethesda Research Labs) with TBE buffer (purchased from Sigma Chemicals). Fragments were extracted from gel slices either with a Prep-A-Gene® Kit (Bio-Rad) or by following phenol extraction procedures known in the art. The sliced gel was suspended in Tris-saturated phenol (Ultra-pure phenol, Bethesda Research Labs), incubated at room temperature for 5 minutes, incubated in a dry ice/ethanol bath for 5 minutes, and spun in a microfuge for five minutes. The aqueous layer was removed and saved. Then, 400 μl TE buffer (10 mM Tris, 1 mM EDTA) was added, the extraction repeated, and the DNA was again ethanol precipitated.

When proteins had to be removed from the desired sequences, the solutions were either passed through a protein binding Millipore Ultrafree-MC 0.45 micron Immobilon-P filter, or extracted with phenol and ethanol precipitated.

F. Cloning Polynucleotide Sequence into Vector

The polynucleotide sequence was then cloned into the pNMHUBpoly vector (obtained from Dr. Tauseef Butt, Smithkline-Beecham Corporation, Philadelphia, Pa.). FIG. 2 shows the restriction map of the pNMHUBpoly vector. Cloning dsTHL 94 into pNMHUBpoly results in libraries encoding 27 amino acid fusions to ubiquitin; the libraries are referred to by the prefix LIB27 to denote fusion size.

pNMHUBpoly constructed in pUC, contains the lambda $P_L$ promoter, a cIIL ribosome binding site, the human ubiquitin gene, and multiple cloning sites [See Ecker, et al., *J. Biol. Chem.*, 262:14213–14221 (1987); Monia, et al., *J. Biol. Chem.*, 264:4093–4103 (1989)]. When the polynucleotide sequence is cloned into the poly site and expressed in *E. coli*, a ubiquitin-fusion protein is produced [See, generally, *Methods in Enzymology*, Vol. 152, pp. 661–673 (1987)]. The novel polypeptides translated from the polynucleotide sequence are then cleaved from the carboxyl terminus of ubiquitin by processing with commercially available rabbit reticulocyte lysate. [Butt, et al., *Proc. Natl. Acad. Sci.*, 86:2540–2544 (1989)]. Alternatively, ubiquitin was cleaved using ubiquitin hydrolase [obtained from Keith Wilkinson, Emory University, Department of Biochemistry, Atlanta, Ga.].

G. Competent Cell Preparation and Transformation

*E. coli* strains MM294 (C1+for DNA production) and AR68 (temperature sensitive C1, for protein expression) obtained from ATCC, were grown in standard bacteria culture broth and were made competent by the hexamine cobalt chloride method described in *Current Protocols in Molecular Biology* (John Wiley & Sons).

Transformation of MM294 and AR68 was carried out by using heat-shock methods.

H. Protein Detection and Purification

Ubiquitin-fusion proteins were expressed in AR58 *E. coli* following the heat shock induction (at 42° C.) of pNMHUBpoly's lambda promoter. Cultures were grown at 42° C. for 1 to 2 hours, harvested by centrifugation, resuspended in TE buffer, and sonicated on ice.

The disruptate was then spun in a Sorvall SS34 rotor at 10K rpm for 30 minutes, and the supernatant was centrifuged in a Beckman Ti50 rotor at 39K rpm for 90 minutes. The high-speed supernatant was used to isolate protein.

Purification of ubiquitin and ubiquitin-fusion proteins was carried out with an FPLC system (Pharmacia®) using a Q-sepharose Fast Flow ion exchange column (about 10 cm bed height in an XK 50 column) and a Sephadex® G-50 gel permeation column (HR16/50). Ubiquitin and fusion proteins passed through the Q-sepharose column equilibrated with 20 mM Tris-HCl, pH 7.5, 50 mM NaCl, 0.03% sodium azide. The fractions containing desired protein were pooled, lyophilized, dissolved in water, and loaded on the G-50 column (equilibrated in 150 mM ammonium bicarbonate). G-50 fractions were pooled and lyophilized to yield protein of between 95 and 99% purity.

Ubiquitin and ubiquitin-fusion proteins were assayed by Western blot using as a primary antibody, SK0591B9.5, a mouse monoclonal antibody raised against human ubiquitin obtained from Dr. Tauseef Butt, SmithKline-Beecham Corp., Philadelphia, Pa. Electrophoresis was performed in a Bio-Rad Mini Protean II apparatus. Proteins were electroblotted onto Millipore Immobilon-P transfer membrane in a Transblot SD Semi-Dry Transfer Cell (Bio-Rad). All Western blot reagents, including the secondary antibody, alkaline phosphatase-conjugated goat anti-mouse IgG, were purchased from Bio-Rad.

Denaturing gels (12% or 15% acrylamide) were run at 150 volts for approximately 45 minutes, soaked in transfer buffer (30 minutes) and blotted at 20 volts for 40 minutes as recommended by the manufacturer. The blots were autoclaved for 15 minutes to enhance the antibody binding to ubiquitin. The blots were then blocked for 30 minutes in a 4% solution of powdered milk, followed by incubation with primary antibody for at least 4 hours and secondary antibody for 1 to 2 hours. Finally, the blots were washed in Tris-buffered saline and Tween 20-Tris-buffered saline and exposed to color development reagents.

Figure 6A:
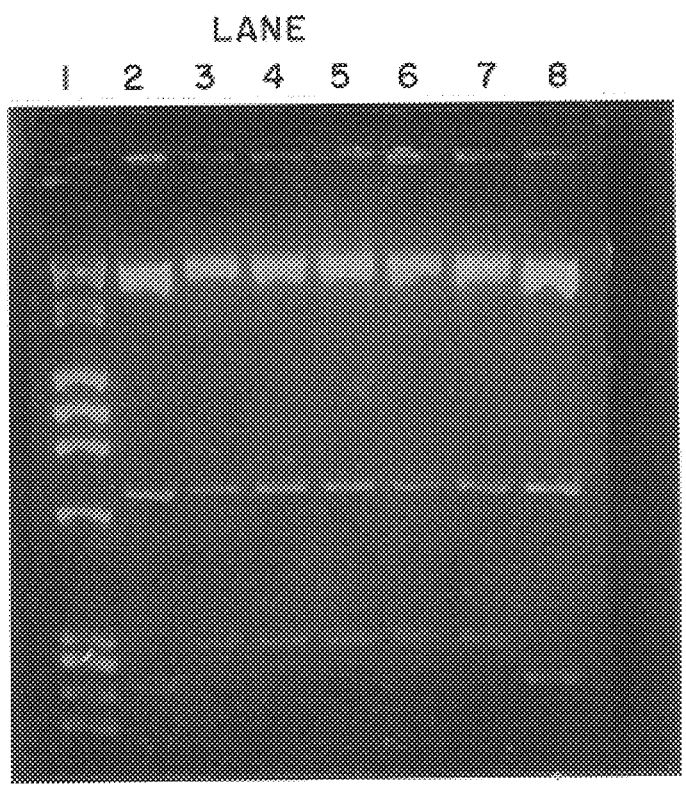
FIGS. 6A–6B show DNA fragments resulting from the EcoRI and BglII co-digest of pNMHUBpoly (lanes 2a, 2b, 8a, and 8b) and ten clones from LIB27-3.27-831 (lanes 3–7a and 3–7b). Lanes 1a and 1b contain DNA size markers. The increase in the molecular weights of the small fragments in lanes 3–7a and 3–7b compared to the pNMHUBpoly lanes demonstrates the insertion of DNA into the clones.
Figure 6B:
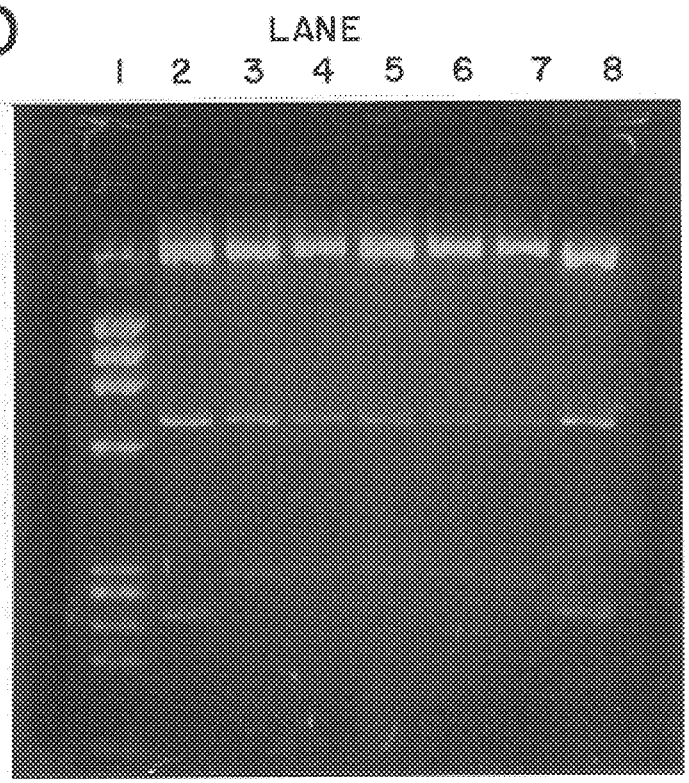

As shown in FIG. 6, plasmid isolated from ten individual clones out of a library of 831 (LIB27-3.27-831) clones was shown to contain insert by restriction mapping. The production of recombinant protein of molecular weight greater than ubiquitin was demonstrated in several individual clones by Western blotting using SK0591B9.5, an anti-ubiquitin monoclonal antibody.

Example 3

The constant region sequences, THL 18, THL 21, and THL 24, and the sequences THL 132 and THL 152, identified below, were synthesized, purified, and amplified according to the procedures described in Example 2. The repeating pattern of nucleotides referred to as $N_1$, $N_2$ and $N_3$ in THL 132 and THL 152 represent the pre-determined proportions of nucleotides as described in Examples 1 and 2.

THL 24 and THL 21 were used as constant regions for THL 152 in the PCR amplification production of double-stranded THL 152 ("dsTHL 152"). THL 18 and THL 21 were used for producing dsTHL 132 ("dsTHL 132"). The PCR products were purified by removing the mineral oil and following manufacturer's instructions in the Prep-A-Gene® kit (Bio-Rad). Approximately 200 ng of each PCR product was purified using 5 µl of binding matrix and two 7.5 µl elutions.

When cloned into pNMHUBpoly, dsTHL 152 provides gene libraries encoding ubiquitin fusion proteins having the following amino acid sequence:

| Met | Gln | Ile | Phe | Val 5 | Lys | Thr | Leu | Thr | Gly 10 | Lys | Thr | Ile | Thr |
|---|---|---|---|---|---|---|---|---|---|---|---|---|---|
| Leu 15 | Glu | Val | Glu | Pro | Ser 20 | Asp | Thr | Ile | Glu | Asn 25 | Val | Lys | Ala |
| Lys | Ile 30 | Gln | Asp | Lys | Glu | Gly 35 | Ile | Pro | Pro | Asp | Gln 40 | Gln | Arg |
| Leu | Ile | Phe 45 | Ala | Gly | Lys | Gln | Leu 50 | Glu | Asp | Gly | Arg | Thr 55 | Leu |
| Ser | Asp | Tyr | Asn 60 | Ile | Gln | Lys | Glu | Ser 65 | Thr | Leu | His | Leu | Val 70 |
| Leu | Arg | Leu | Arg | Gly 75 | Gly | Xaa | Xaa | Xaa | Xaa 80 | Xaa | Xaa | Xaa | Xaa |
| Xaa 85 | Xaa | Xaa | Xaa | Xaa | Xaa 90 | Xaa | Xaa | Xaa | Xaa | Xaa 95 | Xaa | Xaa | Xaa |
| Xaa | Xaa 100 | Xaa | Xaa | Xaa | Xaa | Xaa 105 | Xaa | Xaa | Xaa | Xaa | Xaa 110 | Xaa | Xaa |
| Asp | Pro | | | | | | | | | | | | |

[seq id no 10]

These gene libraries were referred to generally as "LIB38" because they encode an additional 38 amino acids fused to ubiquitin.

dsTHL 132 was then cloned into LIB38 DNA, producing 71 amino acid additions, and having the following amino acid sequence:

| Met | Gln | Ile | Phe | Val 5 | Lys | Thr | Leu | Thr | Gly 10 | Lys | Thr | Ile | Thr |
|---|---|---|---|---|---|---|---|---|---|---|---|---|---|
| Leu 15 | Glu | Val | Glu | Pro | Ser 20 | Asp | Thr | Ile | Glu | Asn 25 | Val | Lys | Ala |
| Lys | Ile 30 | Gln | Asp | Lys | Glu | Gly 35 | Ile | Pro | Pro | Asp | Gln 40 | Gln | Arg |
| Leu | Ile | Phe 45 | Ala | Gly | Lys | Gln | Leu 50 | Glu | Asp | Gly | Arg | Thr 55 | Leu |

-continued

| Ser | Asp | Tyr | Asn | Ile | Gln | Lys | Glu | Ser | Thr | Leu | His | Leu | Val |
|-----|-----|-----|-----|-----|-----|-----|-----|-----|-----|-----|-----|-----|-----|
|     |     |     | 60  |     |     |     |     | 65  |     |     |     |     | 70  |
| Leu | Arg | Leu | Arg | Gly | Gly | Xaa | Xaa | Xaa | Xaa | Xaa | Xaa | Xaa | Xaa |
|     |     |     |     | 75  |     |     |     |     | 80  |     |     |     |     |
| Xaa | Xaa | Xaa | Xaa | Xaa | Xaa | Xaa | Xaa | Xaa | Xaa | Xaa | Xaa | Xaa | Xaa |
| 85  |     |     |     |     | 90  |     |     |     |     | 95  |     |     |     |
| Xaa | Xaa | Xaa | Xaa | Xaa | Xaa | Xaa | Xaa | Xaa | Xaa | Xaa | Xaa | Xaa | Xaa |
|     | 100 |     |     |     |     | 105 |     |     |     |     | 110 |     |     |
| Asp | Leu | Xaa | Xaa | Xaa | Xaa | Xaa | Xaa | Xaa | Xaa | Xaa | Xaa | Xaa | Xaa |
|     |     | 115 |     |     |     |     | 120 |     |     |     |     | 125 |     |
| Xaa | Xaa | Xaa | Xaa | Xaa | Xaa | Xaa | Xaa | Xaa | Xaa | Xaa | Xaa | Xaa | Xaa |
|     |     |     | 130 |     |     |     |     | 135 |     |     |     |     | 140 |
| Xaa | Xaa | Xaa | Xaa | Xaa | Asp | Pro |     |     |     |     |     |     |     |
|     |     |     |     | 145 |     |     |     |     |     |     |     |     |     |

[seq id no 11]

By cloning an additional dsTHL 132 sequence into "LIB71" DNA, libraries are produced having 104 amino acids fused to the ubiquitin proteins. This process can be repeated to incrementally add 33 amino acids to the fusion proteins.

Figure 3:
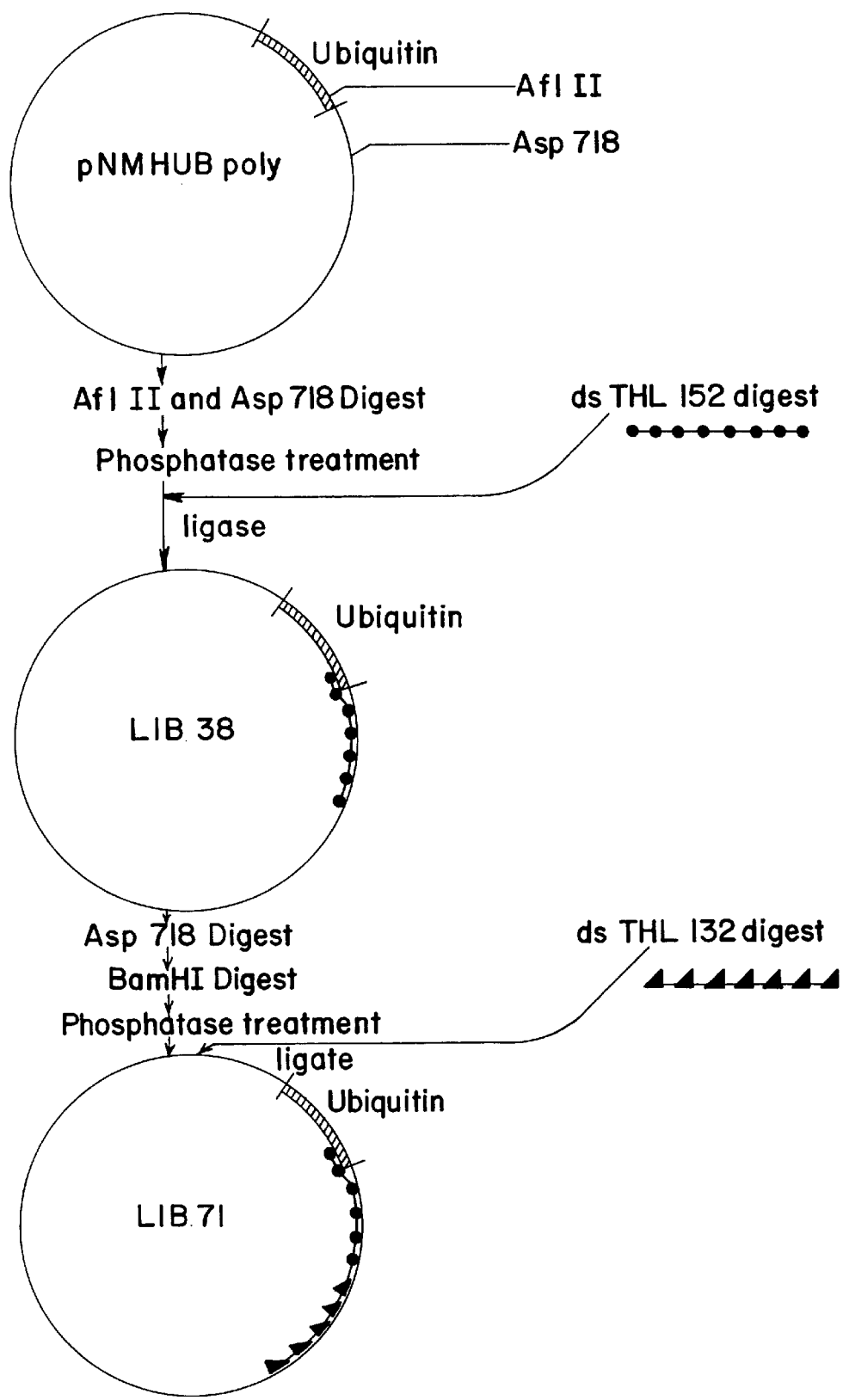
FIG. 3 shows the overall scheme by which dsTHL 152, is cloned into the pNMHUBpoly vector to produce libraries of 38 amino acid fusions and dsTHL 132 is cloned into the LIB38 DNA to produce libraries of 71 amino acid fusions.

FIG. 3 shows the overall cloning scheme of the libraries encoded by THL 152 and THL 132. Specifically, 16 µg pNMHUBpoly was digested with 10 U AflII (New England Biolabs) and 2 U Asp 718 (Boehringer Mannheim Biochemicals) in a total of 40 µl containing 10 mM Tris-HCl (pH 8.0), 5 mM $MgCl_2$, 100 mM NaCl, 1 mM 2-mercaptoethanol, and 100 µg/ml BSA for 18 hours at 37° C. The digested pNMHUBpoly was then dephosphorylated by adding 2 U calf intestinal alkaline phosphatase (Promega) and $ZnCl_2$ to 1 mM and incubating the solution at 37° C. for 1 hour. The solution was then heat-killed at 75° C. for 10 minutes, and passed through a protein-binding filter (Ultrafree-Probind purchased from Millipore) to remove the enzymes.

Simultaneously, approximately 100 ng dsTHL 152 was digested with 5 U AflII and 1 U Asp 718 in 30 µl under the conditions described above for the pNMHUBpoly digest. The solution was then heat-killed at 75° C. for 10 minutes, and passed through a protein-binding filter.

Six batches of digested, dephosphorylated pNMHUBpoly (350 ng each) and digested dsTHL 152 (10 ng each) were then ligated in a total volume of 40 µl, at 16° C. for 2 hours using the manufacturer's instructions. (TaKaRa Biochemicals). Also, bacterial cells were transformed with 90–180 ng ligated DNA, following the method described in Example 2.

Figure 4:
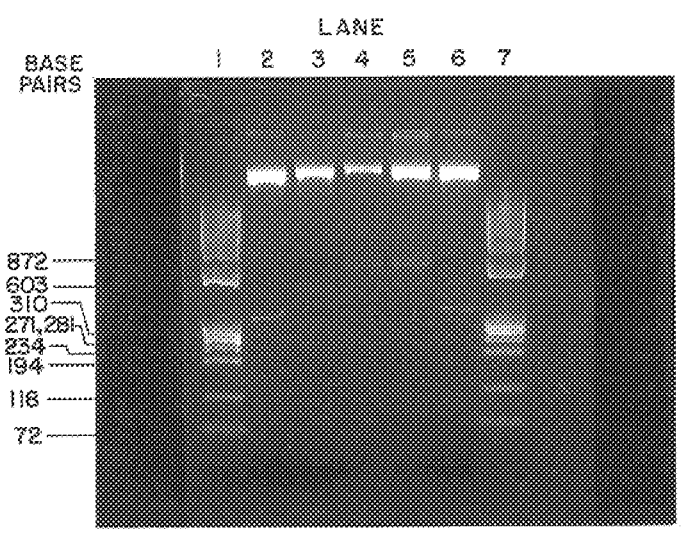
FIG. 4 shows the DNA fragments resulting from the BstXI and BamHI co-digest of pNMHUBpoly (lanes 2 and 6), LIB38-10.11-30,000 (lane 3), LIB71-11.20-19,000 (lane 4) and LIB71-11.20-2100 (lane 5). Lane 1 contains DNA size markers. The incremental increase in the molecular weights of the small fragment in lanes 2–4 demonstrates the insertion of DNA in increasing size.
Figure 5:
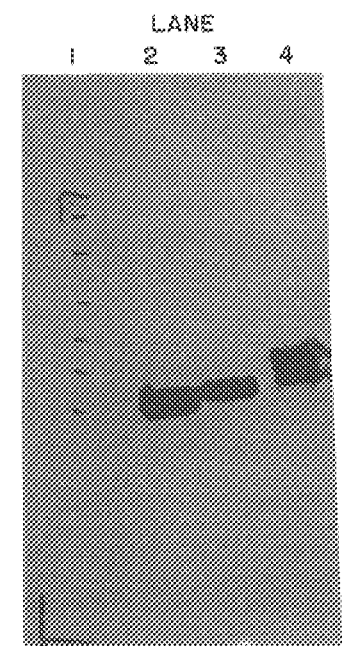
FIG. 5 shows a Western blot of a polyacrylamide gel demonstrating incremental increases in the molecular weight of the protein recognized by SK0591B9.5, an anti-ubiquitin monoclonal antibody. Lane 1 contains molecular weight marker proteins. Lane 2 contains ubiquitin from bovine red blood cells. Lane 3 contains raw, *E. coli* extract from cells transformed with p38-10.11a (a single clone which produces a 38 amino acid fusion to ubiquitin). Lane 4 contains extract from *E. coli* transformed with p71-9.23u (a clone producing a 71 amino acid fusion with ubiquitin). Note that ubiquitin and ubiquitin fusions may run slightly faster than the marker proteins, probably due to incomplete unfolding of ubiquitin.

Two gene libraries were constructed. One of the libraries contained 3600 clones (LIB38-10.11-3600). The other library contained 30,000 clones (LIB38-10.11-30,000). As shown in FIG. 4, lane 3, restriction mapping demonstrated the existence of the insert in the purified library DNA. When expressed in E. coli AR68 cells, LIB38 clones produced a protein of expected size which is recognized by SK0591B9.5, an anti-ubiquitin monoclonal antibody (see lane 3, FIG. 5).

Next, the construction of a library of clones containing 71 amino acid fusions to ubiquitin proceeded with LIB38-10.11-30,000 DNA that was purified using Qiagen maxiprep (Qiagen, Inc.). Approximately 6 µg LIB38 DNA was digested with 40 U Asp 718 (Boehringer Mannheim Biochemicals) at 37° C. for 18 hours in 50 µl containing 33 mM Tris-acetate (pH 7.9), 10 mM magnesium acetate, 66 mM potassium acetate, and 0.5 mM dithiothreitol. The solution was then heat-killed at 75° C. for 10 minutes, and passed through a protein binding filter. 20 U BamHI (Boehringer Mannheim Biochemicals) was then added. The solution was incubated at 37° C. for 2 hours, followed by the addition of 20 U calf intestinal alkaline phosphatase (New England Biolabs) plus $ZnCl_2$ to 1 mM. The solution was incubated for 1 hour at 37° C., heat-killed at 75° C. for 10 minutes, and then passed through a protein-binding filter.

Simultaneously, approximately 150 ng dsTHL 132 was prepared and purified as described above. dsTHL 132 DNA was digested with 40 U BqlII (Promega) and 40 U Asp 718 (Boehringer Mannheim Biochemicals) in 25 µl, at 37° C. for 18 hours in 10 mM Tris-HCl (pH 8.0), 5 mM $MgCl_2$, 100 mM NaCl, and 1 mM 2-mercaptoethanol. The solution was then heat-killed at 75° C. for 10 minutes and passed through a protein-binding filter.

The digested, dephosphorylated LIB38 DNA (approximately 200 ng each in 5 batches) was ligated to digested dsTHL 132 (12 ng each batch) in a total volume of 40 µl at 16° C. for 30 minutes according to manufacturer's instructions (TaKaRa Biochemicals). Also, bacterial cells were transformed with approximately 212 ng ligated DNA, following the method described in Example 2.

Two libraries were constructed. One of the libraries contained 2100 clones (LIB71-11.20-2100) and the other library contained 19,000 clones (LIB71-11.20-19,000). As shown in FIG. 4, lanes 4 and 5, restriction mapping demonstrated the existence of the insert in the purified library DNA. Further, LIB71 clones produced a protein of expected size which is recognized by SK0591B9.5, an anti-ubiquitin monoclonal antibody (see lane 4, FIG. 5).

In summary, useful methods and materials for producing libraries of diverse nucleotide sequences and libraries of polypeptides encoded thereby. Although specific embodiments and examples have been described herein, it should be born in mind that these have been provided by way of explanation and illustration and that the present invention is not limited thereby. Modifications which are within the skill in the art to make are considered to lie within the scope of the invention as defined by the claims, including all equivalents.

TABLE 2

Example Enzyme Family For Generation Of Compatible Overhangs
Amino Acids Encoded

| Enzyme | Recognition Sequence | Frame 1' | Frame 2' | Frame 3' |
|---|---|---|---|---|
| AccI | GTCGAC | Cys, Arg, Leu, Pro<br>Ser, Gly--Arg--His, Gln, Arg | Val--Asp | Leu, Ser, Trp, Pro, Gln<br>Arg, Met, Thr, Lys, Val--Ser-Thr<br>Ala, Glu, Gly, stop |
| AhaII | GACGTC | Arg, Gly  Leu, Pro<br>stop--Arg--His, Gln, Arg | Asp--Val | Leu, Ser, Trp, Pro, Gln<br>Arg, Met, Thr, Lys, Val--Thr-Ser<br>Ala, Glu, Gly, stop |
| BstBI | TTCGAA | Phe, Leu  Ile, Met, Thr<br>Ile, Val--Arg--Asn, Lys, Ser, Arg | Phe--Glu | Phe, Ser, Tyr, Cys, Leu,<br>Pro, His, Ile, Thr, Asn--Ser--Asn, Lys<br>Ser, Val, Ala, Asp, Gly |
| ClaI | ATCGAT | Tyr, His  Phe, Leu, Ser, Tyr<br>Asn, Asp--Arg--Cys, Trp, stop | Ile, Asp | Leu, Ser, Pro, Gln, Arg,<br>Ile, Thr, Lys, Val, Ala--Ser--Ile, Met<br>Glu, Gly, stop |
| NarI | GGCGCC | Trp  Leu, Pro<br>Arg, Gly--Arg--His, Gln, Arg | Gly--Ala | Leu, Ser, Trp, Pro, Gln,<br>Arg, Met, Thr, Lys, Val--Ala--Pro<br>Ala, Glu, Gly, stop |
| HfnPI | GCGC | Leu, Ser, Trp, Pro, Gln<br>Arg, Met, Thr, Lys, Val--Arg<br>Ala, Glu, Gly, stop | Cys, Arg<br>Ser, Gly--Ala | Leu, Pro<br>Ala--His, Gln, Arg |
| HpaII | CCGG | Phe, Ser, Tyr, Cys, Leu<br>Pro, His, Arg, Ile, Thr--Arg<br>Asn, Val, Ala, Asp, Gly | Ser, Pro<br>Thr, Ala--Gly | Val, Ala<br>Pro--Asp, Glu, Gly |
| MaeII | ACGT | Leu, Ser, Pro, Gln, Arg<br>Ile, Thr, Lys, Val, Ala--Arg<br>Glu, Gly, stop | Tyr, His<br>Asn, Asp--Val | Phe, Leu, Ser, Tyr<br>Thr--Cys, Trp, stop |
| TaqI | TCGA | Phe, Ser, Tyr, Cys, Leu,<br>Pro, His, Ile, Thr, Asn--Arg<br>Ser, Val, Ala, Asp, Gly | Phe, Leu<br>Ile, Val--Asp, Glu | Ile, Met, Thr<br>Ser--Asn, Lys, Ser, Arg |

Reading frame 2 placed the codon division between the central CG pair of the palindrome. Frames 1 and 3 are shifted one base to the left and right, respectively. For example, the recognition sequence for Acc I is GTC GAC, thus in frame 1 it reads NGT, CGA, CNN; frame 2 gives GTC, GAC; and frame 3 reads NNG, TCG, ACN wherein N is an undertermined base.

---

What is claimed is:

1. A method for producing a library of diverse nucleotide sequences, comprising the steps of:

providing a first constant region comprising a first restriction enzyme site;

sequentially coupling nucleotides to the constant region in the 3' to 5' direction to form a coding sequence of desired length, wherein the nucleotides for each coupling step are provided in pre-determined proportions of A, T, C, and G, corresponding to pre-determined proportions of amino acids, the pre-determined proportions of amino acids chosen so as to produce similarities between an amino acid profile of a functional protein and the amino acid profile of a polypeptide encoded by the coding sequence; and coupling to said coding sequence a second constant region comprising a second restriction enzyme site.

2. The method of claim 1 further comprising the step of amplifying the sequences.

3. The method of claim 1 wherein the pre-determined proportions of A, T, C, and G comprise from about 6% to 15% T, from about 18% to 27% C, from about 29% to 36% A and from about 31% to 41% G in the first position; from about 23% to 29% T, from about 31% to 26% C, from about 20% to 31% A and from about 21% to 27% G in the second position; and from about 60% to 74% T or C, 0% A and from about 26% to 40% G in the third position.

4. A method for producing a library of vectors with diverse nucleotide sequences, comprising the steps of:

providing a first constant region comprising a first restriction enzyme site;

sequentially coupling nucleotides to the constant region in the 3' to 5' direction to form a coding sequence of desired length, wherein the nucleotides for each coupling step are provided in pre-determined proportions of A, T, C, and G, corresponding to pre-determined proportions of amino acids, the pre-determined proportions of amino acids chosen so as to produce similarities between an amino acid profile of a functional protein and the amino acid profile of a polypeptide encoded by the coding sequence;

coupling to said coding sequence a second constant region comprising a second restriction enzyme site;

digesting the sequences with a first and second restriction enzyme; and introducing the digested sequences into a vector.

5. The method of claim 4 wherein after the coding sequence is coupled to the constant regions, the sequences are amplified.

6. The method of claim 4 wherein the first and second restriction enzymes are different enzymes.

7. The method of claim 4 wherein, after digesting the sequences, a plurality of the digested sequences are ligated to each other to thereby form longer diverse sequences which are then introduced into a vector.

8. A vector produced by the method of claim 4, comprising:

a) a promoter which permits transcription of a synthetic coding sequence;

b) a start codon; and c) a synthetic coding sequence comprising sequentially coupled nucleotides in pre-determined proportions of A, C, T, and G based upon a known amino acid profile and operatively linked to the promoter.

9. The vector of claim 8 wherein the vector is a protein-fusion vector.

10. The vector of claim 9 wherein the protein-fusion vector is pNMHUBpoly.

11. The method of claim 4 wherein the pre-determined proportions of A, T, C, and G comprise from about 6% to 15% T, from about 18% to 27% C, from about 29% to 36% A and from about 31% to 41% G in the first position; from about 23% to 29% T, from about 31% to 26% C, from about 20% to 31% A and from about 21% to 27% G in the second position; and from about 60% to 74% T or C, 0% A and from about 26% to 40% G in the third position.

12. A method for producing a library of diverse polypeptides, comprising the steps of:

providing a first constant region comprising a first restriction enzyme site;

sequentially coupling nucleotides to the constant region in the 4' to 5' direction to form a coding sequence of desired length, wherein the nucleotides for each coupling step are provided in pre-determined proportions of A, T, C, and G, corresponding to pre-determined proportions of amino acids, the pre-determined proportions of amino acids chosen so as to produce similarities between an amino acid profile of a functional protein and the amino acid profile of a polypeptide encoded by the coding sequence;

coupling to said coding sequence a second constant region comprising a second restriction enzyme site;

amplifying the sequences;

digesting the sequences with a first and second restriction enzyme;

introducing the digested sequences into a vector; and providing proper conditions for the vector to express the sequences.

13. The method of claim 12 wherein the pre-determined proportions of A, T, C, and G comprise from about 6% to 15% T, from about 18% to 27% C, from about 29% to 36% A and from about 31% to 41% G in the first position; from about 23% to 29% T, from about 31% to 26% C, from about 20% to 31% A and from about 21% to 27% G in the second position; and from about 60% to 74% T or C, 0% A and from about 26% to 40% G in the third position.

* * * * *

UNITED STATES PATENT AND TRADEMARK OFFICE
CERTIFICATE OF CORRECTION

PATENT NO. : 5,869,295
DATED : February 9, 1999
INVENTOR(S) : Thomas H. LaBean et al.

It is certified that error appears in the above-identified patent and that said Letters Patent is hereby corrected as shown below:

In claim 12, line 6, replace "4'" with --3'--.

Signed and Sealed this

Thirtieth Day of November, 1999

Attest:

Q. TODD DICKINSON

*Attesting Officer*     *Acting Commissioner of Patents and Trademarks*